US011262090B2

United States Patent
Lundgreen et al.

(10) Patent No.: US 11,262,090 B2
(45) Date of Patent: Mar. 1, 2022

(54) HUMIDIFIER WITH AUTOMATIC DRAIN INTERVAL DETERMINATION

(71) Applicant: DRI-STEEM Corporation, Eden Prairie, MN (US)

(72) Inventors: James M. Lundgreen, Lakeville, MN (US); Kenneth D. Shull, Eden Prairie, MN (US)

(73) Assignee: DRI-STEEM Corporation, Eden Prairie, MN (US)

( * ) Notice: Subject to any disclaimer, the term of this patent is extended or adjusted under 35 U.S.C. 154(b) by 194 days.

(21) Appl. No.: 16/251,908

(22) Filed: Jan. 18, 2019

(65) Prior Publication Data

US 2019/0226704 A1  Jul. 25, 2019

Related U.S. Application Data

(60) Provisional application No. 62/619,704, filed on Jan. 19, 2018.

(51) Int. Cl.
*F24F 11/30* (2018.01)
*F24F 11/63* (2018.01)
(Continued)

(52) U.S. Cl.
CPC ............. *F24F 11/30* (2018.01); *F24F 6/02* (2013.01); *F24F 11/0008* (2013.01);
(Continued)

(58) Field of Classification Search
CPC ........ F24F 11/30; F24F 11/0008; F24F 11/63; F24F 16/9017; F24F 6/02;
(Continued)

(56) References Cited

U.S. PATENT DOCUMENTS 2,328,538 A  9/1943  Furlong
2,555,528 A  6/1951  Angelery
(Continued)

FOREIGN PATENT DOCUMENTS

CA  2967262  12/2017
CN  101029758 A  9/2007
(Continued)

OTHER PUBLICATIONS

"Conversion of units" Wikipedia published May 29, 2015 accessed at <https://en.wikipedia.org/w/index.php?title=Conversion_of_units &oldid=664581566> (Year: 2015).*
(Continued)

*Primary Examiner* — Stephen Hobson
(74) *Attorney, Agent, or Firm* — Merchant & Gould P.C.

(57) ABSTRACT

With respect to atmospheric steam generating humidifiers, the present disclosure resolves the problem of end-users not adjusting the drain interval of the humidifier by using an electronic controller to automatically choose an appropriate drain interval without requiring any user input. The electronic controller accomplishes this by receiving input data from a sensor that measures a water quality parameter, automatically determining a drain interval based on the received data, and sending an output control signal to a drain water control valve to execute a drain event in accordance with the drain interval. In some examples, the electronic controller utilizes a look-up table correlating the water quality parameter to a total dissolved solids or cycles of concentration value.

13 Claims, 3 Drawing Sheets

(51) Int. Cl.
*G06F 16/901* (2019.01)
*F24F 6/02* (2006.01)
*F24F 11/00* (2018.01)
*F24F 6/00* (2006.01)

(52) U.S. Cl.
CPC .......... *F24F 11/63* (2018.01); *G06F 16/9017* (2019.01); *F24F 2006/008* (2013.01)

(58) Field of Classification Search
CPC ...... F24F 2006/008; F24F 11/61; F24F 6/025; G01N 33/1853; C02F 2209/05; C02F 1/008; C02F 2209/10; C02F 2209/006
See application file for complete search history.

(56) References Cited

U.S. PATENT DOCUMENTS

| | | | |
|---|---|---|---|
| 3,801,077 A | 4/1974 | Pearson | |
| 4,034,571 A * | 7/1977 | Bollinger | B60N 3/18 62/244 |
| 4,054,122 A | 10/1977 | Reed | |
| 4,146,775 A * | 3/1979 | Kirchner | F24F 6/025 392/327 |
| 4,285,302 A * | 8/1981 | Kelly | F22B 37/565 122/382 |
| 4,294,223 A | 10/1981 | Montague | |
| 4,360,368 A * | 11/1982 | Lyon | F24F 6/14 96/364 |
| 4,382,173 A | 5/1983 | Howard-Liecester | |
| 5,161,488 A | 11/1992 | Natter | |
| 5,292,904 A | 8/1994 | Sawada et al. | |
| 5,349,946 A | 9/1994 | McComb | |
| 5,435,151 A * | 7/1995 | Han | B60H 1/3233 62/272 |
| 5,816,496 A | 10/1998 | Kovacs | |
| 6,058,718 A * | 5/2000 | Forsberg | C02F 1/008 62/125 |
| 6,182,453 B1 * | 2/2001 | Forsberg | C02F 9/005 62/125 |
| 6,370,878 B1 | 4/2002 | Dean et al. | |
| 6,397,788 B2 | 6/2002 | Besik | |
| 6,508,208 B1 * | 1/2003 | Frasure | F24H 1/207 122/380 |
| 6,684,648 B2 * | 2/2004 | Faqih | E03B 3/28 62/93 |
| 6,755,037 B2 * | 6/2004 | Engel | F24F 3/1405 62/177 |
| 6,997,004 B1 * | 2/2006 | Pittman | B60H 1/00207 62/244 |
| 7,623,711 B2 * | 11/2009 | Berkner | G06K 9/00463 382/176 |
| 7,623,771 B2 * | 11/2009 | Lentz | F22B 37/56 392/386 |
| 7,826,725 B2 * | 11/2010 | Wolff | F24F 6/18 392/402 |
| 7,913,433 B2 * | 3/2011 | Jiang | D06F 75/12 38/77.9 |
| 9,091,497 B2 | 7/2015 | Schwendinger et al. | |
| 2004/0040322 A1 * | 3/2004 | Engel | F24F 3/1405 62/177 |
| 2005/0126199 A1 * | 6/2005 | Akkad | C02F 9/005 62/291 |
| 2006/0249099 A1 | 11/2006 | Besik | |
| 2007/0000906 A1 * | 1/2007 | Kaastra | A47J 27/21 219/441 |
| 2009/0255323 A1 | 10/2009 | Butt et al. | |
| 2010/0025311 A1 * | 2/2010 | Jones | C02F 1/048 210/149 |
| 2011/0140291 A1 * | 6/2011 | Hoglund | F24F 6/18 261/128 |
| 2011/0232775 A1 | 9/2011 | Chale et al. | |
| 2012/0199330 A1 | 8/2012 | Maurer et al. | |
| 2012/0221198 A1 * | 8/2012 | Kohavi | B60H 1/3233 701/36 |
| 2012/0247135 A1 * | 10/2012 | Fakieh | F24F 3/1405 62/129 |
| 2013/0186748 A1 | 7/2013 | Yoon et al. | |
| 2015/0090581 A1 | 4/2015 | Saifutdinov et al. | |
| 2016/0083936 A1 * | 3/2016 | Martin | B01D 5/006 261/128 |
| 2017/0023276 A1 | 1/2017 | Aktiengesellschaft | |
| 2017/0334736 A1 | 11/2017 | Lam et al. | |
| 2017/0356663 A1 | 12/2017 | Couperthwaite et al. | |
| 2019/0226699 A1 | 7/2019 | Lundgreen et al. | |
| 2019/0257533 A1 * | 8/2019 | Tak | F24F 5/00 |

FOREIGN PATENT DOCUMENTS

| | | |
|---|---|---|
| CN | 103328031 A | 9/2013 |
| DE | 2512233 A1 | 9/1976 |
| DE | 3145302 A1 | 5/1983 |
| EP | 1260772 A1 | 11/2002 |
| EP | 1703220 A1 | 9/2006 |
| EP | 3339729 A1 | 6/2018 |
| EP | 3258180 | 1/2020 |
| GB | 628351 | 8/1949 |
| JP | 59210215 | 11/1984 |
| JP | 59210234 | 11/1984 |
| JP | 2014085027 A | 5/2014 |
| JP | 5950788 | 7/2016 |
| KR | 100607854 | 7/2006 |
| KR | 100816042 B1 | 3/2008 |
| KR | 101243698 | 3/2013 |
| KR | 1020170003813 | 1/2017 |
| SU | 1760239 A1 | 9/1992 |

OTHER PUBLICATIONS

Search Report and Written Opinion corresponding to PCT/US2019/014269 dated May 14, 2019.
NORTEC-2014 GS Install and Operations Manual, Jan. 2014.
NORTEC-GS Install-Pulsed Dual Fill Valve, Nov. 2015.
Extended European Search Report for EP19741948.4 dated Sep. 21, 2021.

* cited by examiner

HUMIDIFIER WITH AUTOMATIC DRAIN INTERVAL DETERMINATION

RELATED APPLICATIONS

This application claims priority to U.S. Provisional Patent Application Ser. No. 62/619,704, filed on Jan. 19, 2018, the entirety of which is incorporated by reference herein.

BACKGROUND

Steam is often used to humidify buildings for comfort and process applications. If a building does not have a steam boiler or has insufficient steam capacity, a steam generating humidifier can be used to supply steam for humidification purposes. Atmospheric pressure steam humidification generators typically use electricity or gas (natural gas or propane) to heat and boil water at atmospheric pressure.

Typically, as steam exits a humidifier, the water level in the tank drops. Unlike small, portable residential steam humidifiers, commercial and industrial steam humidifiers have an electronic controller, water level sensing capabilities, and valves to automatically re-fill the tank. In some applications, the sequence of steam generation and re-filling the tank is repeated while the humidifier is operating.

As this process occurs, mineral concentration steadily increases with each re-fill since the exiting steam is generally pure water vapor, thus leaving the minerals in the liquid water. Commercial and industrial humidifiers can employ automatic drain events to remove the concentrated minerals in an effort to reduce scale accumulation and minimize corrosion. In more sophisticated systems, the amount of steam generated and hence water consumed is recorded by the electronic controller. For example, the electronic controller may be programmed to drain a portion or the entire tank after creating a certain number of pounds of steam or after a certain number of gallons or tanks of water are used. The amount of draining is typically programmable by the end-user.

SUMMARY

Mineral concentration of potable water varies dramatically with geographic location, water source, and water treatment. Humidifiers operating with high mineral content water typically require a higher drain interval or more draining (as a percentage of the water entering the humidifier) than those operating with low mineral content water. For example, a low drain interval of 1% means 1% of the water that enters the humidifier is drained out, thus concentrating the water 100 times, or, a cycle of concentration (COC) of 100. A high drain interval of 25% means 25% of the water that enters is drained out, thus concentrating the water 4 times, or a COC of 4.

The automatic drain events are typically programmable by the end-user, who is expected to know the mineral concentration of the water supplied to the humidifier and adjust the drain interval programming appropriately. However, end users are often unaware, uninterested, or too busy to determine their water type and navigate through the controller menu to find and adjust the drain interval appropriately. As a result, most steam humidifiers are likely operating with default drain intervals as shipped by the manufacturer. In many cases this means the drain interval is either excessive or insufficient, thus incurring excessive water consumption and reduced performance or additional scale accumulation and risk of corrosion, respectively.

In some humidifier applications the mineral concentration of the supply water, or Total Dissolved Solids (TDS), changes seasonally or with economics, influencing changes to the supply water source. In these cases it is even more unlikely that end-users are repeatedly changing the drain intervals to match the changing supply water TDS.

The present disclosure resolves the problem of end-users not adjusting the drain interval by using an electronic controller to automatically choose an appropriate drain interval without requiring any user input.

In one aspect of the disclosure, an atmospheric steam generating humidifier is disclosed. The humidifier can include an unpressurized water storage tank, a steam outlet extending from the water storage tank for allowing steam generated within the water storage tank to exit the water storage tank, a water drain outlet extending from the water storage tank to allow water to be drained from the water storage tank, a heating element for converting water stored within the tank to steam at atmospheric pressure, a drain water control valve in fluid communication with the water drain outlet, and a sensor for sensing a water quality parameter associated with water stored within the water storage tank. In one example, the humidifier also includes an electronic controller which receives input data from the sensor and sends output control signals to the drain water control valve. The electronic controller sends an output control signal to the drain water control valve at a selected or calculated drain interval to drain the water storage tank based on input data received from the sensor.

In some examples, the water quality sensor is a total dissolved solids meter and the water quality parameter is water total dissolved solids.

In some examples, the water quality sensor is an electrical conductivity probe and the water quality parameter is water electrical conductivity expressed in counts.

In some examples, the drain interval is based on one or more of an amount of steam generated by the humidifier, a number of tanks of steam generated by the humidifier, or a cycles of concentration of the water within the tank.

In some examples, the electronic controller includes a look-up table correlating the water quality parameter to a cycles of concentration value or total dissolved solids of the tank.

In some examples, the electronic controller multiplies a volume of the tank by the cycles of concentration value to calculate a drain interval defined in terms of steam produced by the humidifier.

In some examples, the steam produced by the humidifier is expressed within the controller as pounds of steam generated or a number of tanks of water generated to steam.

In some examples, the sensor includes a plurality of sensors.

In some examples, the plurality of sensors includes three sensors having different lengths.

In one aspect of the disclosure, a method for operating an atmospheric steam generating humidifier is disclosed. The method can include the steps of sensing a value of a water quality parameter at a sensor in fluid communication with an interior volume of a humidifier tank, receiving the sensed value at an electronic controller, selecting or calculating a drain interval based on the sensed value, and operating a drain valve associated with the humidifier tank to drain the humidifier tank at the selected drain interval.

In some examples, the water quality parameter is a value based on electrical conductivity of water within the humidifier tank.

In some examples, the drain interval is based on one or more of an amount of steam generated by the humidifier, a number of tanks of steam generated by the humidifier, or a cycles of concentration of the water within the tank.

In some examples, the step of selecting or calculating the drain interval includes referring to a look-up table correlating the water quality parameter value to a cycles of concentration.

In some examples, the step of selecting or calculating the drain interval includes multiplying a volume of the tank by the cycles of concentration from the look-up table to calculate the drain interval.

In some examples, the drain interval defined in the controller as a total amount of steam produced by the humidifier since the last drain event.

In some examples, the steam produced by the humidifier is expressed within the controller as total pounds of steam generated since the last drain event or a total number of tanks of water generated to steam since the last drain event.

An atmospheric steam generating humidifier can include an unpressurized water storage tank, a steam outlet extending from the water storage tank for allowing steam generated within the water storage tank to exit the water storage tank, a water drain outlet extending from the water storage tank to allow water to be drained from the water storage tank, a heating element for converting water stored within the tank to steam at atmospheric pressure, a fill water control valve in fluid communication with an inlet of the water storage tank, a drain water control valve in fluid communication with the water drain outlet, a first water senor within the water storage tank for sensing a first water level within the water storage tank, a second water sensor within the water storage tank for sensing a second water level within the water storage tank different from the first water level, wherein one or both of the first and second water sensors is a water quality sensor for sensing a water quality parameter associated with water stored within the water storage tank, and an electronic controller which receives input data from the first and second sensors and sends output control signals to the fill and drain water control valves, wherein the electronic controller sends an output control signal to the drain water control valve at a selected or calculated drain interval to drain the water storage tank based on input data received from at least one of the first and second sensors, and sends an output control signal to the fill water control valve based upon input data received from at least one of the first and second sensors.

In some examples, the water quality sensor is either a total dissolved solids meter and the water quality parameter is water total dissolved solids; or an electrical conductivity probe and the water quality parameter is water electrical conductivity expressed in counts.

In some examples, the drain interval is based on one or more of an amount of steam generated by the humidifier, a number of tanks of steam generated by the humidifier, or a cycles of concentration of the water within the tank; the electronic controller includes a look-up table correlating the water quality parameter to a cycles of concentration value or total dissolved solids of the tank; and multiplies a volume of the tank by the cycles of concentration value to calculate a drain interval defined in terms of steam produced by the humidifier, wherein the steam produced by the humidifier is expressed within the controller as pounds of steam generated or a number of tanks of water generated to steam.

A variety of additional aspects will be set forth in the description that follows. The aspects can relate to individual features and to combinations of features. It is to be understood that both the forgoing general description and the following detailed description are exemplary and explanatory only and are not restrictive of the broad inventive concepts upon which the examples disclosed herein are based.

BRIEF DESCRIPTION OF THE DRAWINGS

The accompanying drawings, which are incorporated in and constitute a part of the description, illustrate several aspects of the present disclosure. A brief description of the drawings is as follows.

DETAILED DESCRIPTION

Figure 1:
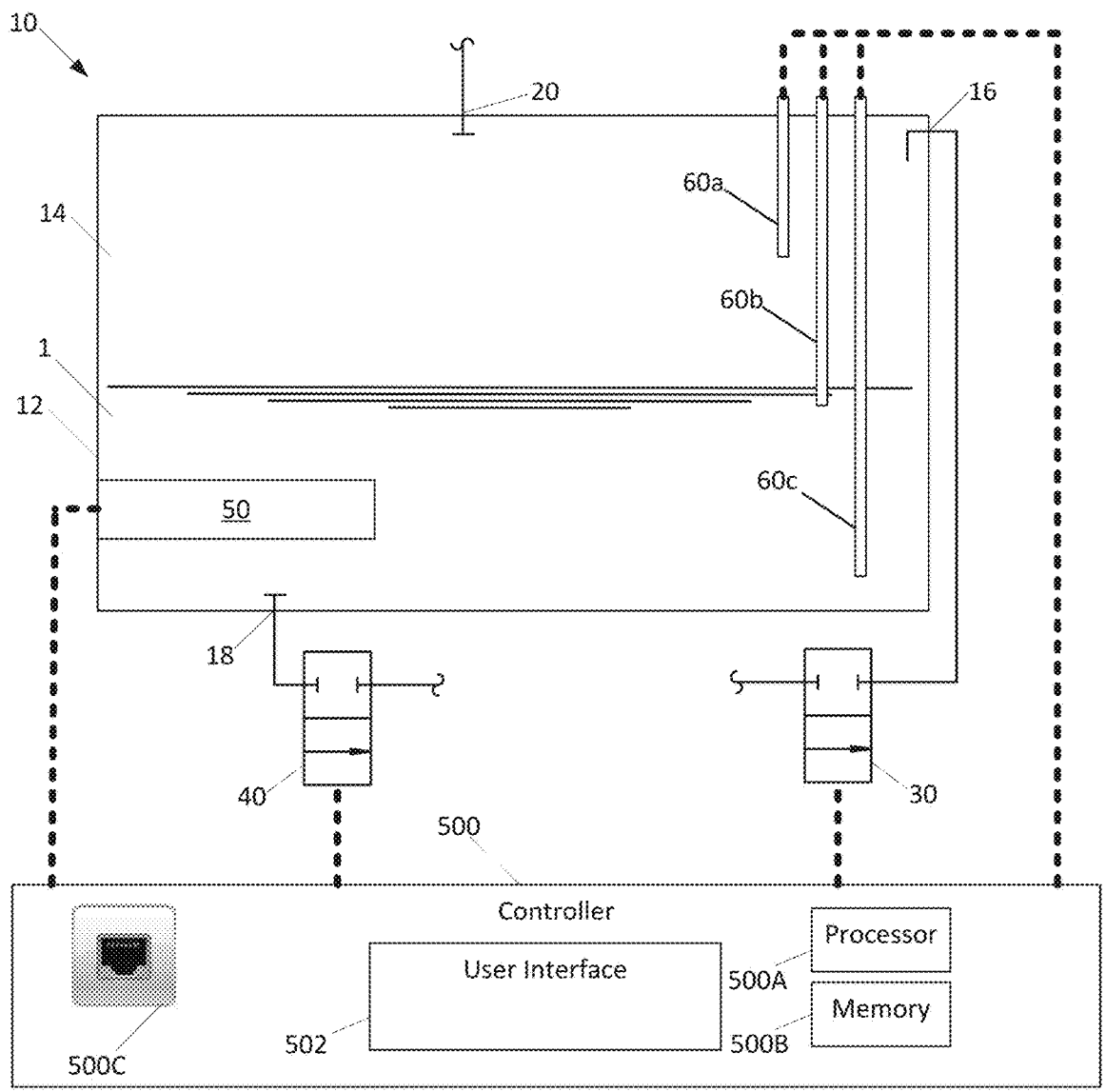
FIG. 1 is a schematic view of an atmospheric steam humidifier and control system having features that are examples of aspects in accordance with the principles of the present disclosure, the evaporative media system being usable in the air handling system shown in FIG. 1.

Various examples will be described in detail with reference to the drawings, wherein like reference numerals represent like parts and assemblies throughout the several views. Reference to various examples does not limit the scope of the claims attached hereto. Additionally, any examples set forth in this specification are not intended to be limiting and merely set forth some of the many possible examples for the appended claims. Referring to the drawings wherein like reference numbers correspond to like or similar components throughout the several figures.

General Description

Referring to FIG. 1, an atmospheric steam humidifier 10 and an electronic controller 500 for operating the humidifier 10 are presented. As shown, the humidifier 10 includes a water storage tank 12 defining an interior volume 14 for holding a volume of water 1. In one aspect, the water storage tank 12 includes a water inlet 16 such that the storage tank can be filled with make-up water. The water storage tank 12 also includes a drain outlet 18 such that water can be drained from the water storage tank 12. The water storage tank 12 further includes a steam outlet 20 through which steam generated within the water storage tank 12 can exit for delivery to a steam distribution system.

The atmospheric steam humidifier 10 is also shown as including a heating element 50 disposed within the water storage tank 12. In one example, the heating element 50 is an immersed electric resistive heating element and the electronic controller 500 sends a signal to energize the heating element 50 to heat the water in the tank to generate steam. Heating element 50 can also be configured as a gas-fired heater, a steam-to-liquid heater, a liquid-to-steam heater, or an electrode-type heater.

As steam is generated by the heating element 50, the water level drops in the tank 12 which results in the need for make-up water to be added to the tank. To add water to the tank 12, a make-up water valve 30 can be provided and controlled by the electronic controller 500. In one example, the control valve 30 includes a fast-fill control valve for rapid filling and a micro-fill control valve for more precise filling at a lower flow rate. In operation, the electronic controller 500 sends a command to open the make-up water valve 30 which allows water to enter the tank from a supply source via the water inlet 16 in the water storage tank 12.

Water can also be drained from the tank through operation of a drain water control valve 40 commanded by the electronic controller 500. As is discussed in more detail later, water from the water storage tank 12 should be drained from the tank periodically to reduce scaling within the interior surfaces water storage tank 12. The drain water control valve 40 is in fluid communication with the tank drain outlet 18 such that when the electronic controller 500 commands the drain water control valve 40 to the open position, water is drained from the water storage tank 12.

Sensors 60*a*, 60*b*, 60*c* (sensors 60) can also be provided within the water storage tank 12. The sensors 60 can be configured to provide data inputs to the electronic controller 500. In one application, sensor 60*a* can be used to identify a maximum-filled water condition to ensure that the make-up water valve does not fill the water storage tank 12 beyond a predetermined level. Likewise, sensor 60*c* can be used to identify a minimum-filled water condition to ensure that the water storage tank 12 has not been drained below a suitable level for operation and to ensure that the water storage tank 12 has been drained sufficiently during a draining operation. Sensor 60*b* can be used to determine a midpoint fill level in the tank 12. As is discussed in more detail later, the sensors 60 can also be used to measure the electrical conductivity of the water within the tank. In one example, one or all of the sensors 60 is configured as an electrical conductivity meter. In one example one or all of the sensors 60 is configured as a total dissolved solids (TDS) meter.

Control System

With continued reference to FIG. 1, the humidifier 10 may also include an electronic controller 500. The electronic controller 500 is schematically shown as including a processor 500A and a non-transient storage medium or memory 500B, such as RAM, flash drive or a hard drive. Memory 500B is for storing executable code, the operating parameters, and the input from the operator user interface 502 while processor 500A is for executing the code. The electronic controller is also shown as including a transmitting/receiving port 500C, such as an Ethernet port for two-way communication with a WAN/LAN related to an automation system. A user interface 502 may be provided to activate and deactivate the system, allow a user to manipulate certain settings or inputs to the controller 500, and to view information about the system operation.

The electronic controller 500 typically includes at least some form of memory 500B. Examples of memory 500B include computer readable media. Computer readable media includes any available media that can be accessed by the processor 500A. By way of example, computer readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the processor 500A.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

The electronic controller 500 is also shown as having a number of inputs/outputs that may be used for implementing the below described draining methods for maintaining water quality within the tank 12 such that scaling is minimized. As mentioned previously, electronic controller 500 provides outputs for energizing the heating element 50, an output for controlling the make-up water fill control valve 30, and an output for controlling a tank drain water control valve 40. Status inputs can be provided for each of the aforementioned control components as well. Additionally, inputs for tank water level and water conductivity via sensors 60 and tank water temperature (not shown) may be provided as well. The controller 500 can also include additional inputs and outputs for desirable operation of the humidifier 10 and related systems.

Process 1000

Figure 2:
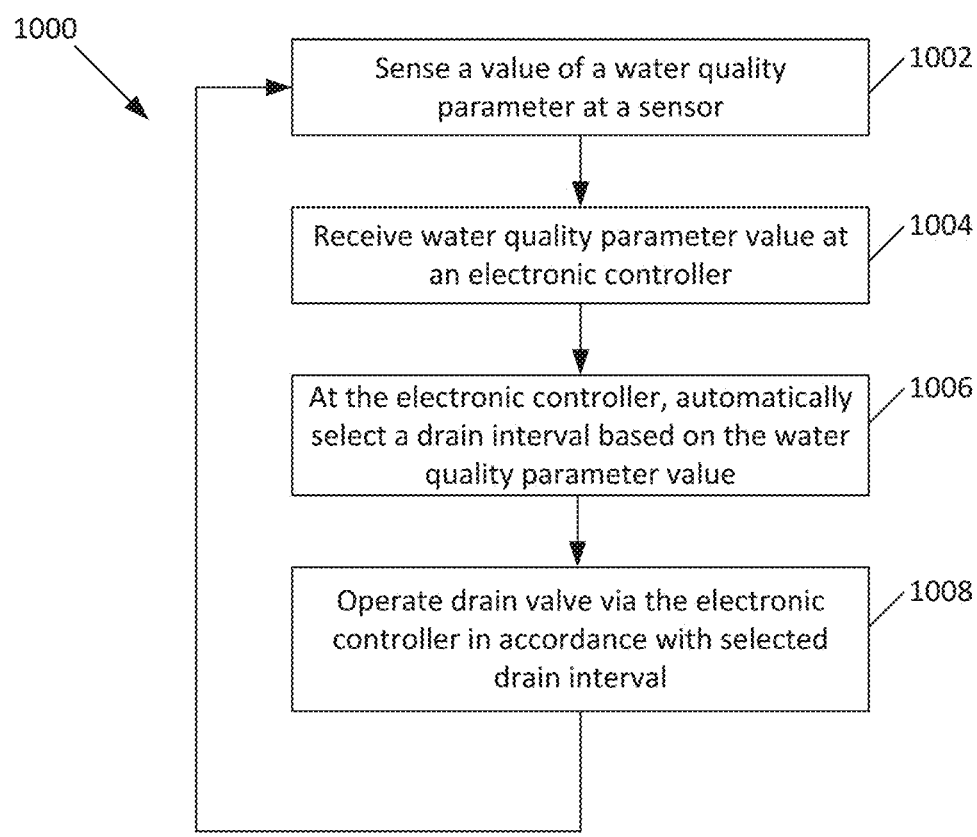
FIG. 2 is a flow diagram for a control process for operating the steam humidifier shown in FIG. 1.

In one aspect, the controller 500 may be programmed to execute an automatic drain control process 1000, as outlined at FIG. 2. The disclosed process 1000 solves the problem of end-users not adjusting the drain interval by using the electronic controller to automatically choose an appropriate drain interval. Electrical conductivity of water increases with mineral concentration. By measuring the electrical conductivity of the water, the mineral concentration is generally known thus allowing an appropriate drain interval to be selected. While there are scenarios, such as excessively high chlorides in supply water, where the best drain interval must still be determined by the end-user, for the majority of applications the automatically chosen drain interval will be superior to the default drain interval that inevitably remains in most humidifiers.

Figure 3:
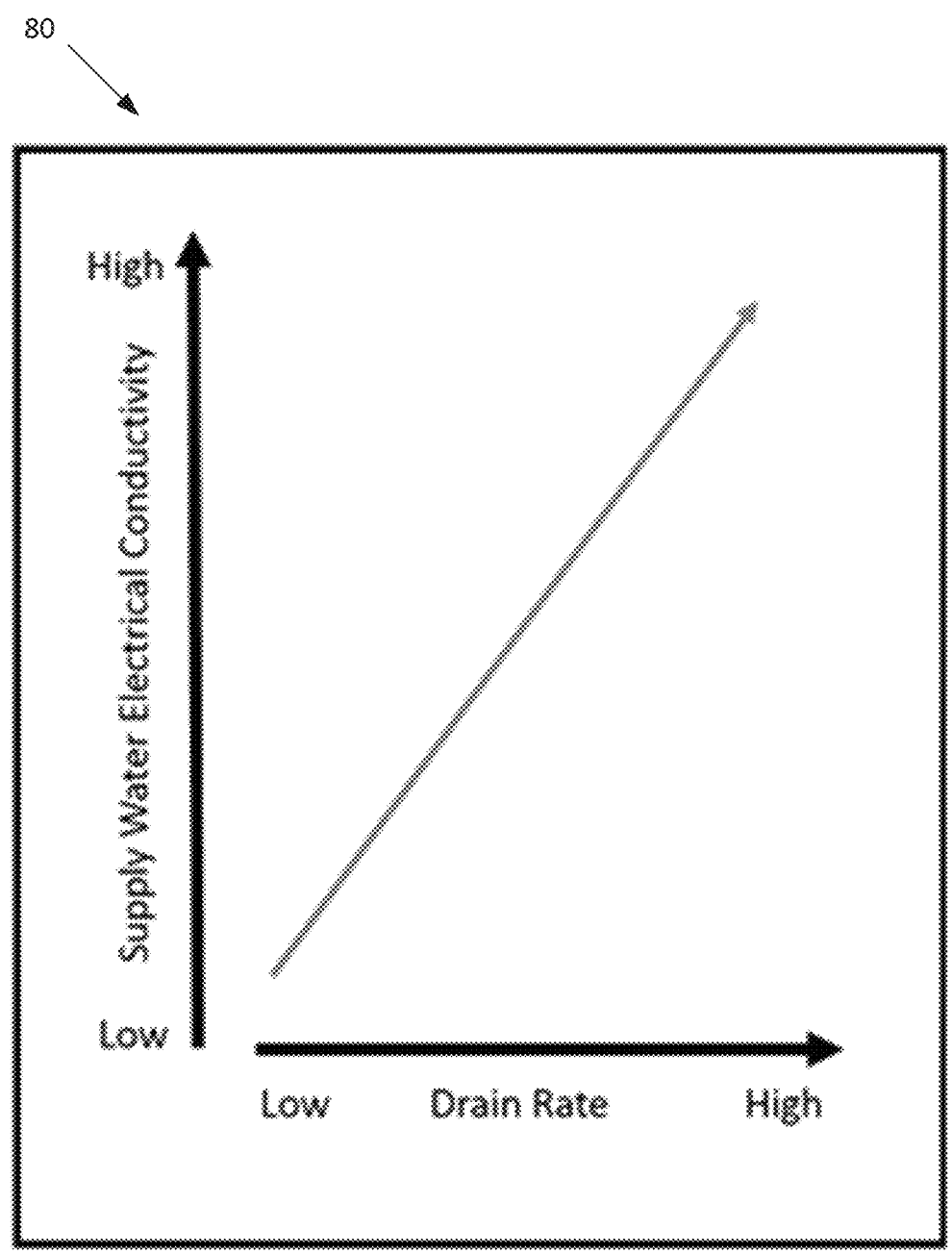
FIG. 3 is a graphical depiction showing a general relationship between supply water electrical conductivity and the drain interval of the humidifier shown in FIG. 1.

In a step 1002, one or more of the sensors 60*a*, 60*b*, 60*c* (generically referred to as sensor 60) is a dedicated sensor for sensing a value of a water quality parameter. In one example, the sensor 60 is a total dissolved solids (TDS) meter and expresses the water quality parameter value in terms of total dissolved solids or electrical conductivity of the water. In one example, the sensor 60 is an electrical conductivity (EC) meter and expresses the water quality parameter value in terms of electrical conductivity. In a step 1004, the electronic controller 500 receives the water quality parameter value data from the sensor 60. In a step 1006, the electronic controller 500 automatically selects a drain interval based on the water quality parameter value received at the electronic controller 500. In one example, step 1006 includes referring to a look-up table that correlates the water quality parameter (e.g. conductivity, TDS) with a drain interval and selecting a drain interval corresponding to the sensed water quality parameter value. In one example, step 1006 includes using a formula defining a relationship (e.g. a curve) between the water quality parameter value (e.g. conductivity, TDS) and the drain interval, and calculating a drain interval based on inputting the sensed water quality parameter value. Referring to FIG. 3, a graph 80 is presented showing a general relationship between water electronic conductivity (i.e. water quality parameter) and a resulting drain interval. As can be seen, the drain interval increases with water electrical conductivity. In a step 1008, the electronic controller 500 operates the drain valve 40 in accordance with the selected or calculated drain interval.

In a preferred embodiment, sensors 60 simultaneously serve as electrical conductivity probes used for detecting the water level within the water storage tank 12 and as water electrical conductivity sensors so appropriate drain intervals can be automatically selected by the electronic controller 500.

Various methods exist regarding the details of measuring the water quality parameter (i.e. electrical conductivity) and controlling the drain intervals. For example, the supply water conductivity can be measured at step 1002 each time an empty tank is filled, following a complete tank drain event, or upon initial fill. The automatically selected drain interval at step 1006 determines when the next drain event occurs at step 1008. The drain interval can be based on the pounds (lbs) of steam created by the humidifier 10, the number of tanks of water converted to steam, or cycles of concentration (COC). With the tank volume pre-programmed into the electronic controller 500, the tanks used or COC is easily determined by the electronic controller 500. For a further explanation of cycles of concentration, refer to U.S. Pat. No. 9,801,964 entitled Evaporative Cycles of Concentration Control and issued on Oct. 31, 2017, the entirety of which is incorporated by reference herein.

In an alternative approach, a drain event can be initiated automatically based on a attaining a conductivity threshold of the tank water. Since the exiting steam is generally free of minerals, the mineral concentration and conductivity of the tank water steadily climbs during operation. Supply water with high mineral content will attain the conductivity threshold sooner (lower COC) than supply water with a low mineral content. In this manner water with higher conductivity/TDS results in an increased drain interval.

Automatic Drain Interval Determination Example

In one example implementation of the disclosed humidifier 10 and process 1000, the electrical conductivity of water is determined using data from the water level sensing conductivity probes 60, which consist of 3 probe lengths, bottom (60c), middle (60b) and top (60a).

Conductivity measurement (i.e. step 1002) for drain interval determination is taken while filling the tank, such as following a new installation, or after a drain event or upon filling the tank to resume humidification following an end-of-season drain (automatic drain after 72 hours of no humidification).

While filling, once the bottom probe detects water, a fast fill valve is closed and a micro-fill valve remains open, thus reducing the fill rate to about 1/10. The water level slowly increases until just contacting the mid probe whereupon the conductivity measurement is immediately recorded by the electronic controller 500 (i.e. step 1004).

This particular electronic water level sensing system produces a range of values, referred to as "counts", from about 14,000 to 0 (i.e. a water quality parameter). The counts can be characterized to determine their relationship to room temperature waters of various conductivities in microsiemens/cm or µS/cm and Total Dissolved Solids (TDS). (2 µS/cm~1 ppm of TDS.), as follows:

~14,0000 counts=air=0 µS/cm of electrical conductance
~7,000 counts=Typical deionized water (DI) ~0.1 µS/cm=0.05 ppm TDS
~4,000 counts=Reverse osmosis water (RO) ~30 µS/cm=15 ppm TDS
~1,500 counts=potable water/RO blend ~70 µS/cm=35 ppm TDS
~900 counts=typical tap water ~200 µS/cm=100 ppm TDS
~800 counts=well water ~700 µS/cm=350 ppm TDS A look-up table can be developed that defines the drain rate, interval or maximum COC for multiple ranges of counts readings from the water level conductivity probes. This look-up table and the water capacity of the tank are programmed into the electronic controller 500. The electronic controller 500 can be configured to record the pounds (lbs) of steam created based on energy used by the humidifier 10. An example look-up table of count ranges and corresponding COC:

>=7,000 counts=150 COC maximum
<6,000 and >=2,500 counts=120 COC maximum
<2,500 and >=1,200 counts=80 COC maximum
<1,200 and >=800 counts=50 COC maximum
<800 counts=20 COC maximum The electronic controller 500 then returns a drain rate, COC or drain interval for a tank capacity, for example a tank capacity of 100 pounds pounds of water. For purposes of illustration, in one example using the filling and sensing procedure described above, the controller 500 records 960 counts. Using the previously described look-up table programmed into the controller, a reading of 960 counts falls between the <b1,200 and >=800 counts range for a maximum COC of 50, which is retrieved from the look-up table and used to calculate the drain interval. The drain interval can be calculated by multiplying 50 COC by the tank capacity of 100 lbs of water, which yields a result of 5,000 lbs. This means that the mineral concentration will be concentrated to the maximum allowable COC of 50 after creating 5,000 lbs of steam or 50 tanks of water boiled off. The controller 500 can display to the end user that the tank will be drained every 5,000 lbs of steam created. Consequently, the controller 500 records the pounds of steam created based on energy used, and drains the tank after creating 5,000 lbs of steam, thus draining upon reaching the maximum COC of 50 (e.g. step 1008).

Upon the next refill assume the probe counts change because the supply water source was changed to RO water and 3,600 counts is recorded upon filling as described using the previously described approach. The electronic controller 500 will then select a new drain rate per the table with COC of 120, thus replacing the previous drain rate COC of 50. The electronic controller 500 will then calculate a drain interval of 12,000 pounds of steam generation (120 COC× 100 lbs tank capacity=12,000 lbs.). Therefore, every 12,000 lbs of steam created the tank will be drained. The RO water has a lower TDS content, therefore less draining is needed. Water and energy savings are thus realized with no impact to scale accumulation or corrosion. Additionally, slightly better performance is realized from fewer interruptions to steam production.

As evidenced in the above example, the electronic controller 500 automatically determines the optimal drain interval for the humidifier 10 without requiring input from the user as to the nature of the water being supplied to the humidifier 10. Thus, the disclosed humidifier 10 and controller 500 represent an improvement over designs which require information inputted by a user for optimal operation.

From the forgoing detailed description, it will be evident that modifications and variations can be made in the aspects of the disclosure without departing from the spirit or scope of the aspects. While the best modes for carrying out the many aspects of the present teachings have been described in detail, those familiar with the art to which these teachings relate will recognize various alternative aspects for practicing the present teachings that are within the scope of the appended claims.

What is claimed is:

1. An atmospheric steam generating humidifier comprising:
   a) an unpressurized water storage tank;
   b) a steam outlet extending from the water storage tank for allowing steam generated within the water storage tank to exit the water storage tank;
   c) a water drain outlet extending from the water storage tank to allow water to be drained from the water storage tank;
   d) a heating element for converting water stored within the tank to steam at atmospheric pressure;
   e) a drain water control valve in fluid communication with the water drain outlet;
   f) a water quality sensor located in the water storage tank and configured for sensing a water quality parameter associated with make-up water stored within the water storage tank during or after a fill event; and
   g) an electronic controller which receives input data from the water quality sensor during or after the fill event, determines a drain interval to drain the water storage tank based on input data received from the sensor relating to the quality of the make-up water, and sends an output control signal to the drain water control valve at the determined drain interval.

2. The atmospheric steam generating humidifier of claim 1, wherein the water quality sensor is a total dissolved solids meter and the water quality parameter is water total dissolved solids.

3. The atmospheric steam generating humidifier of claim 1, wherein the water quality sensor is an electrical conductivity probe and the water quality parameter is water electrical conductivity expressed in counts.

4. The atmospheric steam generating humidifier of claim 1, wherein the drain interval is based on one or more of an amount of steam generated by the humidifier, a number of tanks of steam generated by the humidifier, or cycles of concentration of the water within the tank.

5. The atmospheric steam generating humidifier of claim 1, wherein the electronic controller includes a look-up table correlating the water quality parameter to a cycles of concentration value or total dissolved solids of the tank.

6. The atmospheric steam generating humidifier of claim 5, wherein the electronic controller multiplies a volume of the tank by the cycles of concentration value to calculate the drain interval defined in terms of steam produced by the humidifier.

7. The atmospheric steam generating humidifier of claim 6, wherein the steam produced by the humidifier is expressed within the controller as pounds of steam generated or a number of tanks of water generated to steam.

8. The atmospheric steam generating humidifier of claim 1, wherein the sensor includes a plurality of sensors.

9. The atmospheric steam generating humidifier of claim 8, wherein the plurality of sensors includes three sensors having different lengths.

10. An atmospheric steam generating humidifier comprising:
    a) an unpressurized water storage tank;
    b) a steam outlet extending from the water storage tank for allowing steam generated within the water storage tank to exit the water storage tank;
    c) a water drain outlet extending from the water storage tank to allow water to be drained from the water storage tank;
    d) a heating element for converting water stored within the tank to steam at atmospheric pressure;
    e) a fill water control valve in fluid communication with an inlet of the water storage tank;
    f) a drain water control valve in fluid communication with the water drain outlet;
    g) a first water senor within the water storage tank for sensing a first water level within the water storage tank;
    h) a second water sensor within the water storage tank for sensing a second water level within the water storage tank different from the first water level;
    i) wherein one or both of the first and second water sensors is a water quality sensor for sensing a water quality parameter associated with water stored within the water storage tank; and
    j) an electronic controller which receives input data from the first and second water sensors after a fill event, determines a drain interval to drain the water storage tank based on input data received from at least one of the first and second water sensors relating to the quality of the stored water, and sends an output control signal to the drain water control valve at the determined drain interval.

11. The atmospheric steam generating humidifier of claim 10, wherein the water quality sensor is either:
    a) a total dissolved solids meter and the water quality parameter is water total dissolved solids; or
    b) an electrical conductivity probe and the water quality parameter is water electrical conductivity expressed in counts.

12. The atmospheric steam generating humidifier of claim 10, wherein the drain interval is based on one or more of an amount of steam generated by the humidifier, a number of tanks of steam generated by the humidifier, or cycles of concentration of the water within the tank.

13. The atmospheric steam generating humidifier of claim 10, wherein the electronic controller further comprises:
    a) a look-up table correlating the water quality parameter to a cycles of concentration value or total dissolved solids of the tank; and
    b) multiplies a volume of the tank by the cycles of concentration value to calculate the drain interval defined in terms of steam produced by the humidifier, wherein the steam produced by the humidifier is expressed within the controller as pounds of steam generated or a number of tanks of water generated to steam.

* * * * *